United States Patent [19]

Gennaro et al.

[11] Patent Number: 4,597,951

[45] Date of Patent: Jul. 1, 1986

[54] STRONTIUM-82/RUBIDIUM-82 GENERATOR

[75] Inventors: Gerald P. Gennaro, East Brunswick; Paul S. Haney, Sayreville, both of N.J.

[73] Assignee: E. R. Squibb & Sons, Inc., Princeton, N.J.

[21] Appl. No.: 641,230

[22] Filed: Aug. 16, 1984

[51] Int. Cl.[4] ...................... A61K 43/00; C22B 26/10; C01F 11/00

[52] U.S. Cl. .......................................... 423/2; 423/6; 252/645

[58] Field of Search ............... 250/432 PD; 423/2, 6; 252/645

[56] References Cited

U.S. PATENT DOCUMENTS

| | | | |
|---|---|---|---|
| 3,953,567 | 4/1976 | Grant et al. | 423/2 |
| 4,400,358 | 8/1983 | Neirinckx | 423/2 |
| 4,432,963 | 2/1984 | Bevan | 424/1.1 |

OTHER PUBLICATIONS

Journal of Nuclear Medicine, vol. 20, pp. 961–966, "Radiochemistry and Radiopharmaceuticals", Yano et al.

Journal of Nuclear Medicine, vol. 25, P119, "Cryptate Complexes of Generator Produced Isotopes for Measurement of Blood Flow", Krohn et al.

ACS Symposium Series 241, Chapter 14, "Radionuclide Generators", Krohn et al.

*Primary Examiner*—John F. Terapane
*Assistant Examiner*—Virginia Caress
*Attorney, Agent, or Firm*—Lawrence S. Levinson; Donald J. Barrack

[57] ABSTRACT

Hydroxylapatite, a compound having the formula $$M_{10}(PO_4)_6(OH)_2,$$

wherein M is calcium, strontium, barium, lead, iron, sodium, potassium, zinc, cadmium, magnesium, aluminum or a rare earth metal, as a support medium for strontium-82 in a strontium-82/rubidium-82 parent-daughter radionuclide generator.

10 Claims, No Drawings

STRONTIUM-82/RUBIDIUM-82 GENERATOR

BACKGROUND OF THE INVENTION

In recent years, developments within the field of nuclear medicine have introduced a new dimension to diagnostic cardiology in that radiopharmaceuticals are now used to study myocardial functions using scintigraphy. The function and viability of the heart can now be visualized at rest or under stress without using invasive surgical techniques and with no discomfort or great expense to the patient. The most common radionuclides now in use or under investigation are thallium-201, potassium-43, and various isotopes of rubidium.

Rubidium, an alkali metal analogue of potassium and similar in its chemical and biological properties, is rapidly concentrated by the myocardium. Recent advances in isotope production and instrumentation suggest that the short-lived radionuclide, rubidium-82, is the agent of choice for myocardial imaging as well as for circulation and perfusion studies.

The preferred source of rubidium-82 is from its parent, strontium-82, which can be produced in a cyclotron via rubidium-85 or by the spallation reaction of high energy protons on a molybdenum target. the short half-life of rubidium-82 (75 seconds) makes it necessary to generate rubidium-82 at the location at which it is to be used. This is accomplished using what is known as a parent-daughter radionuclide generator wherein the parent is strontium-82 (half-life 25 days) and the daughter is rubidium-82. Due to the relatively long half-life of strontium-82, it is possible to manufacture a strontium-82rubidium-82 generator, ship it to the user, and have the user elute rubidium-82 as needed.

The physical configuration of a parent-daughter radionuclide generator is well known in the art. In simple terms, it consists of a system comprising a container which holds a support medium onto which is adsorbed the parent radionuclide, inlet means for receiving eluant and outlet means for removing eluate containing the daughter radionuclide.

The prior art dicloses several materials which have been used as a support medium for strontium-82/rubidium-82 generator. U.S. Pat. No. 3,953,567, issued Apr. 27, 1976, discloses a generator utilizing as a support medium a 100–200 mesh resin which is composed for a styrene-divinyl-benzene copolymer with attached immunodiacetate exchange groups. Yano et al., *J. Nucl. Med.*, 20 (9):961–966 (1979), disclose a generator utilizing as a support medium alumina. U.S. Pat. No. 4,400,358, issued Aug. 23, 1983, discloses a generator utilizing as a support medium hydrated, unhydrated and mixtures of the hydrated and unhydrated and mixtures of the hydrated and unhydrated forms of tin oxide, titanium oxide and ferric oxide, and unhydrated polyantimonic acid.

SUMMARY OF INVENTION

In some myocardial diagnostic studies, it is desirable to have the entire rubidium-82 activity in the heart at a given point in time, rather than having part of the rubidium-82 through the heart, part in the heart and part still to enter the heart at a given point in time. To accomplish this, it is necessary to have a strontium-82/rubidium-82 generator which yields high activity rubidium-82 per unit volume of eluate (*i.e.,* a small bolus size of rubidium-82).

Krohn et al., *J. Nucl. Med.,* 25(5): P119 (1984) and ACS Symposium Series 241, Chapter 14 (1984), describe an idea for the preparation of complexes of generator produced short-lived radioisotopes with cyclic polyethers (cryptands) for measurement of blood flow. Current generators employ an isotonic eluant, generally containing sodium chloride. Because of limited selectivity of the cyclic polyethers towards cryptate formation, sodium (and other cations) will compete with the carrier-free rubidium-82. As succinctly stated by Krohn in the ACS Symposium Series reference, "The main problem encountered in synthesis of cryptates has been the presence of other cations such as $Na^+$ and $K^+$ competing for the cryptand."

It has now been forund that a strontium-82/rubidium-82 generator can be prepared using hydroxylapatite (also known as hydroxyapatite) as the support medium onto which the strontium-82 is absorbed. The use of hydroxylapatite as the support medium results in a generator which yields a small bolus of rubidium-82. The generators prepared using hydroxylapatite can be eluted with a variety of eluants, including water, a non-ionic carrier. Other eluants, such as dextrose (a 5% aqueous solution is preferred) or saline (a 0.9% aqueous salt solution is preferred) can also be used.

DETAILED DESCRIPTION OF THE INVENTION

Hydroxylapatite has the general formula $$M_{10}(PO_4)_6(OH)_2, \qquad \text{I}$$

wherein M can be calcium, strontium, barium, lead, iron, sodium, potassium, zinc, cadmium, magnesium, aluminum, or a rare earth metal (lanthanum, cerium, praseodymium, neodymium, promethium, samarium, europium, gadolinium, terbium, dysporosium, holmium, erbium, thulium, ytterbium, lutetium, and hafnium). Preferred for use in this invention is hydroxylapatite having the formula $$Ca_{10}(PO_4)_6(OH)_2. \qquad \text{II}$$

The use of hydroxylapatite as a support medium for strontium-82 in a strontium-82/rubidium-82 generator results in a generator which yields rubidium-82 in a small bolus and which can yield rubidium-82 by elution with water.

The strontium-82/rubidium-82 generator of this invention can be prepared using any of the columns disclosed in the prior art for parent-daughter radionuclide generators. Exemplary columns are disclosed in U.S. Pat Nos. 3,369,121, issued Feb. 13, 1968, 3,440,423, issued Apr. 22, 1969, 3,920,995, issued Nov. 18, 1975, 4,041,317, issued Aug. 9, 1977 and 4,239,970, issued Dec. 16, 1980. The generator columns of the prior art have varying designs, but each comprises (i) a housing for containing a support medium for the parent nuclide; (ii) inlet means for introducing an eluant into the housing and (iii) outlet means for withdrawing the eluated from the housing.

To prepare a strontium-82/rubidium-82 generator of this invention, the hydroxylapatite that is to be used as the support medium is first slurried with the solvent that is to be used as the eluant. The slurry of strontium-82 will preferably have no carrier added (especially no other Group II metals) and will have an approximately neutral pH.

The following examples further describe the preparation of strontium-82/rubidium-82 generators utilizing hydroxylapatite as an adsorbent.

EXAMPLE 1

Preparation of a 5% Dextrose-eluted Generator

1. Hydroxylapatite (fast flow, Behring Diagnostics, LaJolla, Calif.) was slurried in 5% dextrose.

2. To a Bio-Rad column* that is 0.7 centimeters inner diameter and 15 centimeters tall with a fiberglass pad (Millipore, AP-25) in the bottom of the column, hydroxylapaptite was added to a height of 5 centimeters.

*Bio-Rad Laboratories, Richmond, Calif.

3. A fiberglass pad (Millipore, AP-25) was placed on top of the adsorbent bed.

4. One milliliter of strontium-82 (500 μCi) in 5% dextrose was added to the column by gravity followed by an approximately five milliliter wash with 5% dextrose. The wash eluant was collected and counted. Approximately 99.9% of the Sr-82 was retained on the column.

5. The generator was allowed to stand for one hour prior to the first elution.

6. A reservoir of 5% dextrose eluant was connected to the top of the generator.

7. The generator was vacuum eluted with 20 milliliters evacuated sterile collecting vials.

8. Elutions were approximately 10 milliliters each. 9. Elutions were separated by at least 12 minutes.

10. The rubidium-82 yield, elution rate and strontium breakthrough were recorded for each elution and are reported below in Table 1.

TABLE 1

| | 5% Dextrose Eluant | | | |
|---|---|---|---|---|
| Elution Number | Flow Rate (ml/min) | Rb-82 Yield (μCi@EOE*) | Rb-82 Yield (%@EOE) | Sr-82 Breakthrough (fraction/ml) |
| DAY 1 | | | | |
| 1 | 12 | 82.4 | 72 | nil |
| 2 | 10 | 77.4 | 68 | nil |
| DAY 4 | | | | |
| 3 | 4.7 | 72.0 | 69 | nil |
| 4 | 4.6 | 70.2 | 67 | nil |
| 5 | 4.1 | 75.2 | 72 | nil |
| 6 | 4.5 | 80.2 | 76 | nil |
| 7 | 4.5 | 80.2 | 76 | nil |
| 8 | 5.2 | 86.0 | 82 | nil |
| 9 | 4.5 | 86.4 | 82 | nil |
| 10 | 4.5 | 84.8 | 81 | $7.8 \times 10^{-7}$ |
| 11 | 4.4 | 81.0 | 77 | $3.9 \times 10^{-6}$ |
| 12 | 4.8 | 78.6 | 75 | $4.6 \times 10^{-6}$ |
| DAY 5 | | | | |
| 13 | 4.5 | 80.2 | 79 | $5.7 \times 10^{-6}$ |
| 14 | 4 0 | 72.8 | 71 | $1.3 \times 10^{-5}$ |
| 15 | 3 7 | 71.4 | 70 | $2.0 \times 10^{-5}$ |
| 16 | 3.5 | 67.2 | 66 | $3.5 \times 10^{-5}$ |
| 17 | 3.2 | 70.2 | 69 | $5.7 \times 10^{-5}$ |

*@EOE = at end of elution

EXAMPLE 2

Preparation of a Water-eluted Generator

1. Hydroxylapatite (fast flow, Behring Diagnostics, LaJolla, Calif.) was slurried in distilled water.

2. To a Bio-Rad column that is 0.7 centimeters inner diameter and 15 centimeters tall with a fiberglass pad (Millipore, AP-25) in the bottom of the column, hydroxylapatite was added to a height of 5 centimeters.

3. 0.25 Milliliters of strontium-82 (117 μCi) in water was added to he column by gravity followed by an approximate five milliliter wash with distilled water. The wash eluant was collected and counted. Approximately 99.9% of the Sr-82 was retained on the column.

5. The generator was allowed to stand for one and one-half hours prior to the first elution.

6. A reservoir of water eluant was connected to the top of the generator.

7. The generator was vacuum eluted with 20 milliliter evacuated sterile collecting vials.

8. Elutions were approximately 10 milliliters each.

9. Elutions were separated by at least 12 minutes.

10. Total volume eluted—700 milliliters.

11. The rubidium-82 yield, elution rate and strontium breakthrough are recorded for each elution and are reported below in Table 2.

TABLE 2

| | Water Eluant | | | |
|---|---|---|---|---|
| Elution Number (Cumulative Volume) | Flow Rate (ml/min) | Rb-82 Yield (μCi@EOE) | Rb-82 Yield (%@EOE) | Sr-82 Breakthrough (fraction/ml) |
| DAY 1 | | | | |
| 1 (10) | 9.4 | 42.8 | 36.6 | $<2.5 \times 10^{-6}$ |
| 2 (20) | 9.1 | 40.2 | 34.4 | $<2.5 \times 10^{-6}$ |
| 3 (30) | 8.1 | 39.0 | 33.3 | $<2.5 \times 10^{-6}$ |
| 4 (40) | 6.7 | 46.8 | 40.0 | $<2.5 \times 10^{-6}$ |
| 5 (50) | 4.6 | 38.8 | 33.2 | $<2.5 \times 10^{-6}$ |
| 6 (60) | 4.4 | 40.4 | 34.5 | $<2.5 \times 10^{-6}$ |
| DAY 2 | | | | |
| 7 (70) | 4.7 | 50.6 | 44.4 | $<2.5 \times 10^{-6}$ |
| 8 (80) | 4.5 | 43.8 | 38.4 | $<2.5 \times 10^{-6}$ |
| 9 (90) | 4.2 | 42.4 | 37.2 | $<2.5 \times 10^{-6}$ |
| 10 (100) | 4.7 | 40.6 | 35.6 | $<2.5 \times 10^{-6}$ |
| 11 (110) | 4.7 | 37.0 | 32.5 | $<2.5 \times 10^{-6}$ |
| 12 (120) | 4.1 | 36.0 | 31.6 | $<2.5 \times 10^{-6}$ |
| 13 (130) | 4.2 | 35.6 | 31.3 | $<2.5 \times 10^{-6}$ |
| 14 (140) | 4.4 | 34.6 | 30.4 | $<2.5 \times 10^{-6}$ |
| 15 (150) | 4.3 | 36.4 | 31.9 | $<2.5 \times 10^{-6}$ |
| 16 (160) | 3.8 | 40.4 | 35.4 | $<2.5 \times 10^{-6}$ |
| 17 (170) | 4.1 | 37.2 | 32.6 | $<2.5 \times 10^{-6}$ |
| 18 (180) | 4.0 | 36.2 | 31.8 | $<2.5 \times 10^{-6}$ |
| 19 (190) | 3.8 | 31.0 | 27.2 | $<2.5 \times 10^{-6}$ |
| 20 (200) | 3.5 | 31.6 | 27.7 | $<2.5 \times 10^{-6}$ |
| DAY 5 | | | | |
| 21 (300) | 3.0 | 26.4 | 25.1 | $<2.5 \times 10^{-6}$ |
| 22 (400) | 3.1 | 27.2 | 25.9 | $<2.5 \times 10^{-6}$ |
| 23 (500) | 4.3 | 26.0 | 24.8 | $<2.5 \times 10^{-6}$ |
| DAY 6 | | | | |
| 24 (530) | 3.7 | 29.8 | 29.2 | $<2.5 \times 10^{-6}$ |
| 25 (560) | 3.4 | 26.6 | 26.1 | $<2.5 \times 10^{-6}$ |
| 26 (590) | 3.6 | 26.6 | 26.1 | $<2.5 \times 10^{-6}$ |
| 27 (700) | 3.7 | 31.2 | 30.6 | $<2.5 \times 10^{-6}$ |

EXAMPLE 3

Preparation of a 0.9% Saline-eluted Generator

1. Hydroxylapatite (fast flow, Behring Diagnostics, LaJolla, Calif.) was slurried in a pH 7 phosphate buffer the sodium concentration of which was 0.15 M in sodium.*

*The phosphate buffer used in this example contains 0.051 molar (M) phosphate and 0.154 molar (M) sodium, at pH 7. It is made by preparing stock solutions of monobasic and dibasic sodium phosphate, each of which is 0.051 M with respect to the phosphate anion. Each solution contains sodium chloride to the extend that the total sodium content will be 0.154 M. The composition of the buffer is as follows:

monobasic phosphate stock:
- $NaH_2(PO_4).H_20$ 7.039 grams
- NaCl 6.0 grams
- Water Q.S. to 1 liter dibasic phosphate stock:
- $Na_2H(PO_4).7H_2O$ 13.67 grams
- NaCl 3.0 grams Water Q.S. to 1 liter A mixture of approximately 155 ml of monobasic phosphate stock added to 1 liter of dibasic phosphate stock results in a solution of approximately pH 7.

2. To a Bio-Rad column of 0.7 centimeters inner diameter and 15 centimeters length with a fiberglass pad (Millipore, AP-25) in the bottom of the column, hydroxylapatite was added to a height of 6 centimeters. 3. A fiberglass pad (Millipore, AP-25) was placed on top of the adsorbent bed. 4. Four milliliters of strontium-82 (500 μCi) in a phosphate buffer (pH 7, 0.15 M sodium) was added to the column by vacuum aspiration. 5. For each elution, 10 ml of 0.9% sodium chloride was added to the column and the eluant was drawn through the column into a 20 milliliter evacuated sterile collecting vial.

6. Elutions were approximately 10 milliliters each.

7. The rubidium-82 yield, elution rate and strontium breakthrough were recorded for some of the elutions and are reported below in Table 3.

TABLE 3

| Elution Number (Cumulative Volume) | 0.9% Saline Eluant Flow Rate (ml/min) | Rb-82 Yield (μCi @ EOE) | Sr-82 Breakthrough (fraction/ml) |
|---|---|---|---|
| 1 (20) | —* | — | — |
| 2 (30) | 13.3 | 176.5 | — |
| 3 (40) | 15.0 | 185.4 | — |
| 4 (70) | ~10-15 | — | $4.5 \times 10^{-5}$ |
| 5 (100) | ~10-15 | — | $3.2 \times 10^{-4}$ |
| 6 (130) | ~10-15 | — | $5.9 \times 10^{-4}$ |
| 7 (160) | ~10-15 | — | $8.2 \times 10^{-4}$ |
| 8 (190) | ~10-15 | — | $9.4 \times 10^{-4}$ |
| 9 (220) | ~10-15 | — | $1.0 \times 10^{-3}$ |
| 10 (250) | ~10-15 | — | $1.0 \times 10^{-3}$ |
| 11 (280) | ~10-15 | — | $1.1 \times 10^{-3}$ |
| 12 (310) | ~10-15 | — | $1.1 \times 10^{-3}$ |
| 13 (340) | ~10-15 | — | $1.1 \times 10^{-3}$ |
| 14 (370) | ~10-15 | — | $1.0 \times 10^{-3}$ |
| 15 (385) | ~10-15 | — | $1.2 \times 10^{-3}$ |
| 16 (415) | ~10-15 | — | $9.8 \times 10^{-4}$ |
| 17 (445) | ~10-15 | — | $1.0 \times 10^{-3}$ |
| 18 (475) | ~10-15 | — | $9.7 \times 10^{-4}$ |
| 19 (505) | ~10-15 | — | $9.5 \times 10^{-4}$ |
| 20 (535) | ~10-15 | — | $9.2 \times 10^{-4}$ |
| 21 (565) | ~10-15 | — | $9.0 \times 10^{-4}$ |
| 22 (580) | ~10-15 | — | $1.0 \times 10^{-3}$ |

*— = not measured

What is claimed is:

1. A strontium-82/rubidium-82 generator having a support medium for the strontium-82 comprising a compound of the formula $$M_{10}(PO_4)_6(OH)_2,$$

where in M is calcium, strontium, barium, lead, iron, sodium, potassium, zinc, cadmium, magnesium, aluminum or a rare earth metal.

2. A strontium-82/rubidium-82 generator in accordance with claim 1 having a support medium for the strontium-82 comprising a compound of the formula $$Ca_{10}(PO_4)_6(OH)_2.$$

3. A process for preparing rubidium-82 which comprises adsorbing strontium-82 on a support medium comprising a compound of the formula $$M_{10}(PO_4)_6(OH)_2,$$

wherein M is calcium, strontium, barium, lead, iron, sodium, potassium, zinc, cadmium, magnesium, aluminum or a rare earth metal, and eluting rubidium-82 from the support medium with a solvent selected from the group consisting of water, 5% dextrose in water and 0.9% sodium chloride in water.

4. A process in accordance with claim 3 wherein the support medium comprises a compound of the formula $$Ca_{10}(PO_4)_6(OH)_2.$$

5. A process in accordance with claim 3 wherein the rubidium-82 is eluted from the support medium with water.

6. A process in accordance with claim 3 wherein the rubidium-82 is eluted from the support medium with 5% dextrose in water.

7. A process in accordance with claim 3 wherein the rubidium-82 is eluted from the support medium with 0.9% sodium chloride in water. 8. A process in accordance with claim 4 wherein the rubidium-82 is eluted from the support medium with water. 9. A process in accordance with claim 4 wherein the rubidium-82 is eluted from the support medium with 5% dextrose in water. 10. A process in accordance with claim 4 wherein the rubidium-82 is eluted from the support medium with 0.9% sodium chloride in water.

* * * * *